United States Patent [19]

Huxley et al.

[11] Patent Number: 5,068,359

[45] Date of Patent: Nov. 26, 1991

[54] MICROBICIDAL COMPOSITIONS

[75] Inventors: Alica Huxley, Binningen; Walter Kunz, Oberwil; Peter Ackermann, Pfeffingen; Marius Sutter, Basel, all of Switzerland

[73] Assignee: Ciba-Geigy Corporation, Ardsley, N.Y.

[21] Appl. No.: 537,196

[22] Filed: Jun. 12, 1990

[30] Foreign Application Priority Data

Jun. 20, 1989 [CH] Switzerland .................. 2299/89

[51] Int. Cl.$^5$ ............... C17D 333/72; C07D 307/78
[52] U.S. Cl. .................................... 549/58; 549/469; 549/49
[58] Field of Search ............. 549/58, 49, 467

[56] References Cited

U.S. PATENT DOCUMENTS 4,259,338  3/1981  Paioni et al. .................. 514/320
4,737,516  4/1988  Stutz .
4,829,067  5/1989  Jijima .

OTHER PUBLICATIONS

Ricci et al, "Thiophene Derivatives . . . ", CA 66:115525e (1967).
JP59104374-1 (Derwent Abstract).

Primary Examiner—C. Warren Ivy
Assistant Examiner—Celia Chang
Attorney, Agent, or Firm—George R. Dohmann; Edward McC. Roberts

[57] ABSTRACT

Novel benzothiophene and benzofuran derivatives of the general formula I

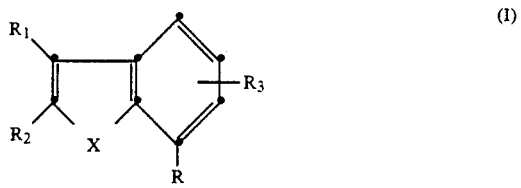

wherein X is oxygen or sulfur, $R_1$ is hydrogen, halogen, $C_1-C_4$alkyl or $C_1-C_4$haloalkyl, $R_2$ is hydrogen, halogen, $C_1-C_4$alkyl or $C_1-C_4$haloalkyl, $R_3$ is hydrogen, $C_1-C_4$alkyl or halogen and R is a 4-cyano-3-pyrrole radical of which the N atom carries one of the following substituents:

A: hydrogen or CO—$R_4$ in which $R_4$ is unsubstituted $C_1C_6$alkyl or $C_1-C_6$alkyl substituted by halogen or by $C_1-C_3$alkoxy; $C_3-C_6$alkenyl, $C_3-C_6$alkynyl, unsubstituted $C_1-C_6$alkoxy or $C_1-C_6$alkoxy substituted by halogen or by $C_1-C_3$alkoxy; $C_3-C_6$alkenyloxy, $C_3-C_6$cycloalkyl or tetrahydrofur2-yl;

B: S-$R_5$ in which $R_5$ is $C_1-C_3$haloalkyl;

C: CH(Y)$R_6$ in which $R_6$ is hydrogen or $C_1-C_8$haloalkyl and Y is hydroxy, halogen or OC(O)$R_7$ in which $R_7$ is $C_1-C_8$alkyl, $C_1-C_8$haloalkyl, $C_2-C_6$alkenyl, 2-tetrahydrofuryl, 2-tetrahydropyranyl or $C_1-C_6$alkoxycarbonyl;

D: $CH_2$-Z in which Z is one of the groups

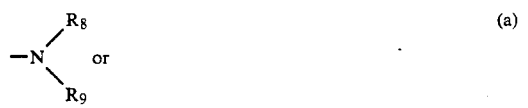

(a)

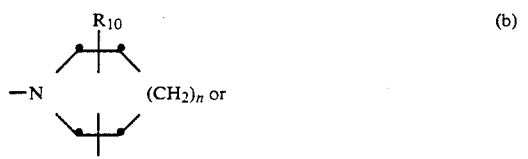

(b)

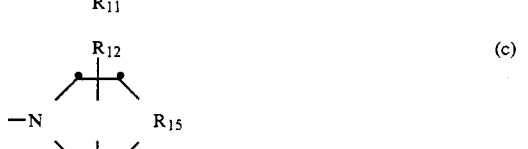

(c)

wherein $R_8$ and $R_9$ are each, independently of the other, hydrogen, unsubstituted $C_1-C_6$alkyl or $C_1-C_6$alkyl substituted by cyano or by $C_1-C_6$alkoxycarbonyl; $C_3-C_6$alkenyl, $C_3-C_6$alkynyl, $C_3-C_7$cycloalkyl, unsubstituted phenyl or phenyl substituted by halogen, by $C_1-C_6$alkyl, by $C_1-C_6$haloalkyl and/or by $C_1-C_6$alkoxy, with the proviso that only $R_8$ or $R_9$ may be hydrogen; $R_{10}$ and $R_{11}$ are each, independently of the other, hydrogen, $C_1-C_6$alkyl or $C_1-C_6$alkoxycarbonyl; $R_{12}$ and $R_{13}$ are each, independently of the other, hydrogen, $C_1-C_6$alkyl or $C_1-C_6$alkoxycarbonyl; and $R_{15}$ is oxygen, sulfur, >C=O or >N—$R_{14}$, wherein $R_{14}$ is hydrogen, $C_1-C_6$alkyl, formyl, $C_1-C_6$alkanoyl or $C_1-C_6$alkoxycarbonyl; and n is one of the numbers 0 or 1.

The novel active ingredients serve to control harmful microorganisms, especially phytophathogenic fungi. They can be used together with suitable formulation adjuvants in the form of compositions, and are suitable also for preventing attack on cultivated plants by harmful microorganisms.

2 Claims, No Drawings

MICROBICIDAL COMPOSITIONS

The present invention relates to novel substituted benzothiophene and benzofuran derivatives, to the preparation thereof, and to microbicidal compositions that contain at least one of those compounds as active ingredient. The invention further relates to the preparation of the said compositions and to the use of the novel active ingredients and compositions for controlling harmful microorganisms, especially plant-destructive fungi.

The compounds of the invention have the general formula I

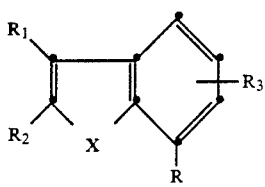

(I)

wherein X is oxygen or sulfur, $R_1$ is hydrogen, halogen, $C_1$–$C_4$alkyl or $C_1$–$C_4$haloalkyl, $R_2$ is hydrogen, halogen, $C_1$–$C_4$alkyl or $C_1$–$C_4$haloalkyl, $R_3$ is hydrogen, $C_1$–$C_4$alkyl or halogen and R is a 4-cyano-3-pyrrole radical of which the N atom carries one of the following substituents:

A: hydrogen or CO—$R_4$ in which $R_4$ is unsubstituted $C_1$–$C_6$alkyl or $C_1$–$C_6$-alkyl substituted by halogen or by $C_1$–$C_3$alkoxy; $C_3$–$C_6$alkenyl, $C_3$–$C_6$-alkynyl, unsubstituted $C_1$–$C_6$alkoxy or $C_1$–$C_6$alkoxy substituted by halogen or by $C_1$–$C_3$alkoxy; $C_3$–$C_6$alkenyloxy, $C_3$–$C_6$cycloalkyl or tetrahydrofur-2-yl;

B: S-$R_5$ in which $R_5$ is $C_1$–$C_3$haloalkyl;

C: CH(Y)$R_6$ in which $R_6$ is hydrogen or $C_1$–$C_8$haloalkyl and Y is hydroxy, halogen or OC(O)$R_7$ in which $R_7$ is $C_1$–$C_8$alkyl, $C_1$–$C_8$haloalkyl, $C_2$–$C_6$-alkenyl, 2-tetrahydrofuryl, 2-tetrahydropyranyl or $C_1$–$C_6$alkoxycarbonyl;

D: $CH_2$-Z in which Z is one of the groups

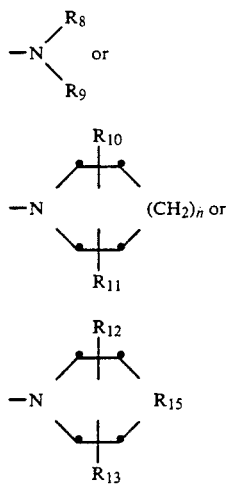

wherein $R_8$ and $R_9$ are each, independently of the other, hydrogen, unsubstituted $C_1$–$C_6$alkyl or $C_1$–$C_6$alkyl substituted by cyano or by $C_1$–$C_6$alkoxycarbonyl; $C_3$–$C_6$alkenyl, $C_3$–$C_6$alkynyl, $C_3$–$C_7$cycloalkyl, unsubstituted phenyl or phenyl substituted by halogen, by $C_1$–$C_6$alkyl, by $C_1$–$C_6$haloalkyl and/or by $C_1$–$C_6$alkoxy, with the proviso that only $R_8$ or $R_9$ may be hydrogen; $R_{10}$ and $R_{11}$ are each, independently of the other, hydrogen, $C_1$–$C_6$-alkyl or $C_1$–$C_6$alkoxycarbonyl; $R_{12}$ and $R_{13}$ are each, independently of the other, hydrogen, $C_1$–$C_6$alkyl or $C_1$–$C_6$alkoxycarbonyl; and $R_{15}$ is oxygen, sulfur, >C=O or >N—$R_{14}$, wherein $R_{14}$ is hydrogen, $C_1$–$C_6$alkyl, formyl, $C_1$–$C_6$alkanoyl or $C_1$–$C_6$alkoxycarbonyl; and n is one of the numbers 0 or 1.

Depending on the number of carbon atoms indicated, alkyl on its own or as a component of another substituent shall be understood as meaning, for example, one of the following groups: methyl, ethyl, propyl, butyl, pentyl, hexyl etc., and the isomers thereof, such as, for example, isopropyl, isobutyl, tert.-butyl, isopentyl etc.. Haloalkyl is a mono- to per-halogenated alkyl substituent, such as, for example, $CH_2Cl$, $CHCl_2$, $CCl_3$, $CH_2Br$, $CHBr_2$, $CBr_3$, $CH_2F$, $CHF_2$, $CF_3$, $CCl_2F$, $CCl_2$—$CHCl_2$, $CH_2CH_2F$, $CI_3$ etc. Throughout this specification halogen denotes fluorine, chlorine, bromine or iodine, preferably fluorine, chlorine or bromine. $C_3$–$C_6$alkenyl is an unsaturated aliphatic radical having one or more double bonds, for example propenyl-(1), allyl, butenyl-(1), butenyl-(2), butenyl-(3), $CH_3CH=CHCH=CH$— etc. Alkynyl shall be understood as meaning an unsaturated aliphatic radical having a maximum of 6 carbon atoms, for example propargyl, butynyl-(2), butynyl-(3) etc.

The compounds of formula I are oils, resins or predominantly crystalline solids that are stable under normal conditions and are distinguished by extremely valuable microbicidal properties. They can be used, for example, in the agricultural sector or related fields, preventatively and curatively for controlling plant-destructive microorganisms. The active ingredients of formula I are distinguished by a high fungicidal activity and problem-free use over a wide concentration range.

Compounds of formula I preferred on account of their microbicidal activity are those in which the pyrrole radical carries at the N atom one of the following radicals: hydrogen or CO—$R_4$ in which $R_4$ is unsubstituted $C_1$–$C_6$alkyl or $C_1$–$C_6$alkyl substituted by halogen or by $C_1$–$C_3$alkoxy; $C_3$–$C_6$-alkenyl, $C_3$–$C_6$alkynyl, unsubstituted $C_1$–$C_6$alkoxy or $C_1$–$C_6$alkoxy substituted by halogen or by $C_1$–$C_3$alkoxy; $C_3$–$C_6$alkenyloxy, $C_3$–$C_6$-cycloalkyl or tetrahydrofur-2-yl.

Of this group, especially preferred are those compounds in which the N atom of the pyrrole carries one of the following radicals: hydrogen or $COR_4$ in which $R_4$ is unsubstituted $C_1$–$C_4$alkyl or $C_1$–$C_4$alkyl substituted by chlorine, by bromine or by $C_1$–$C_3$alkoxy; $C_3$–$C_4$alkenyl, $C_3$–$C_4$alkynyl, unsubstituted $C_1$–$C_4$alkoxy or $C_1$–$C_4$alkoxy substituted by chlorine, by bromine or by $C_1$–$C_3$alkoxy; $C_3$–$C_4$alkenyloxy, $C_3$–$C_6$cycloalkyl or tetrahydrofur-2-yl.

Of the aforementioned active substances attention is drawn to those in which the pyrrole radical carries a hydrogen atom at the N atom, and of the last-mentioned group especially those in which $R_1$ is hydrogen, halogen, $C_1$–$C_2$alkyl or $C_1$–$C_2$haloalkyl, $R_2$ is hydrogen or halogen and $R_3$ is hydrogen.

Of those compounds there are especially active as microbicides those in which $R_1$ is hydrogen or halogen and $R_2$ is hydrogen.

Individual compounds from this group which are to be given special emphasis on account of their activity are 3-(bromobenzothiophen-7-yl)-4-cyanopyrrole and 3-(benzothiophen-7-yl)-4-cyanopyrrole.

The compounds of formula I are prepared in accordance with the invention:

a) in an alkaline medium by cyclising Michael addition of a cyanoacrylic acid, a cyanoacrylic acid ester or a cyanoacrylic acid amide of formula IIa to p-toluenesulfonylmethyl isocyanide, with the removal of p-toluene-sulfinic acid or its salt, in an organic solvent:

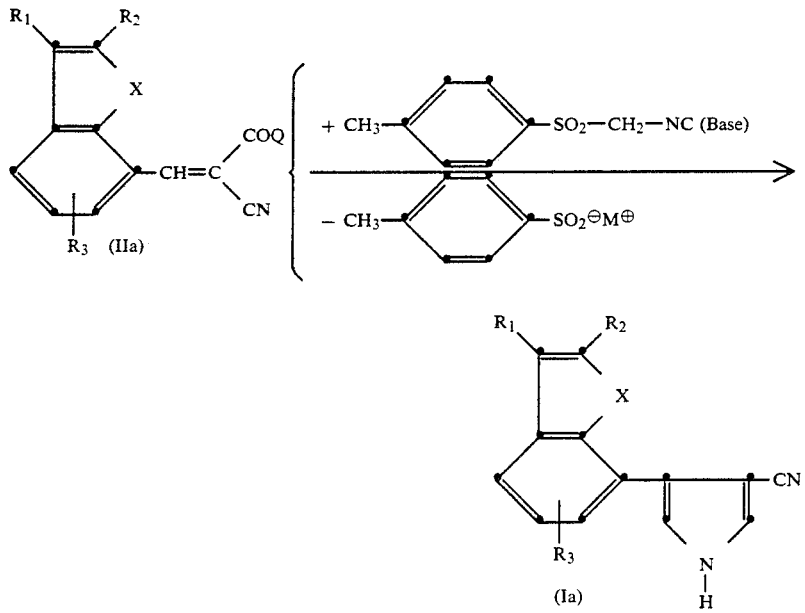

wherein $M^\oplus$ is an alkali or alkaline earth ion and Q OR$_{16}$ or NH$_2$ and R$_{16}$ is hydrogen or C$_1$-C$_4$alkyl, b) by subsequent acylation of compound Ia with a compound of formula III in the presence of an acid-binding agent and, where appropriate, a catalyst, in an organic solvent:

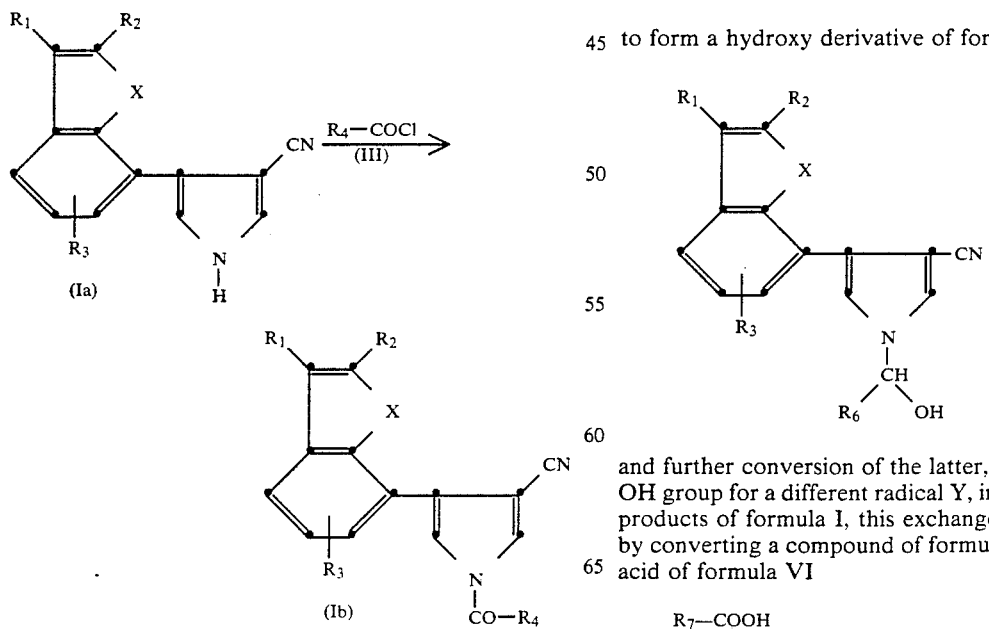

wherein R$_4$ has the meanings given at the beginning for formula I, or c) by sulfenylation of the compound of formula Ia with a reactive acid derivative of a sulfenic acid of formula IV $$R_5S\text{—}OH \qquad (IV)$$

at the pyrrole nitrogen atom in the presence of an acid-binding agent, where appropriate in an organic solvent, R$_5$ having the meanings given at the beginning for formula I, or d) by reaction of the compound of formula Ia with an aldehyde of formula V $$R_6\text{—CHO} \qquad (V)$$

to form a hydroxy derivative of formula Ic

and further conversion of the latter, by exchanging the OH group for a different radical Y, into one of the other products of formula I, this exchange being carried out by converting a compound of formula Ic either with an acid of formula VI $$R_7\text{—COOH} \qquad (VI)$$

or, preferably, with a reactive acid derivative thereof, especially an acid halide, such as, for example, the chloride or bromide, or with its acid anhydride, into an acyloxy product of formula Id

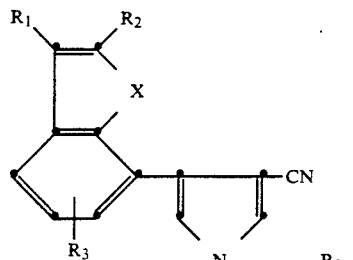

or by first exchanging the OH group in a compound of formula Ic in customary manner for a halogen atom, preferably a chlorine or bromine atom, to obtain the compound of formula Ie

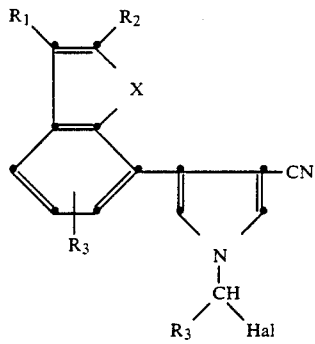

and then, further, converting the halogenated product by reaction with a salt of formula VII $$R_7-COO^{\ominus}M'^{\oplus 1} \quad (VII)$$

into a compound of formula Id, the substituents in formulae Ic, Id, Ie, V, VI and VII having the meanings given for formula I, Hal being halogen and $M'^{\oplus}$ being a metal cation, preferably an alkaline earth metal cation or especially an alkali metal cation, such as, for example, $Ca^{\oplus\oplus}$, $Mg^{\oplus\oplus}$, $Na^{\oplus}$ or $K^{\oplus}$, or e) by reaction of a compound of formula Ia with a compound of formula VIII $$H-Z \quad (VIII)$$

in which Z has the meanings given at the beginning for formula I, either in a protic solvent at temperatures of from 0° to 120° C., preferably at from 20° C. to the reflux temperature, in the presence of a basic or acidic reaction catalyst with formaldehyde; or in an aprotic solvent or in the presence of a basic reaction catalyst at temperatures of from 0° to 120° C., preferably from 20° to 80° C., with 1,3,5-trioxane or paraformaldehyde.

In step a) of the described reaction sequence, according to the invention the cyanoacrylic acid or an ester thereof of formula IIa can be replaced by an acrylonitrile of formula IIb:

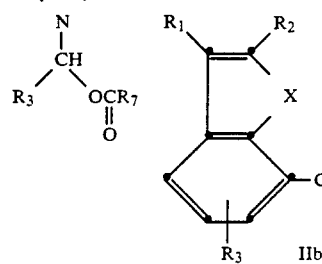

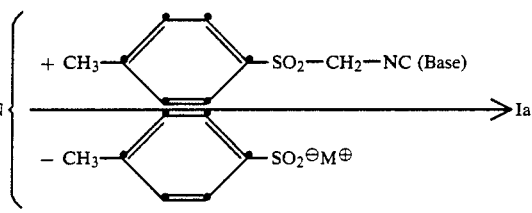

Reaction step (a)

The p-tolylsulfonyl group here is representative of a whole series of groups that are capable of activating the methylene group in the methyl isocyanide radical for a Michael addition reaction. Other preferred examples of groups capable of such activation are benzenesulfonyl, p-chlorobenzenesulfonyl and lower alkylsulfonyl, such as mesyl.

The cycloaddition is carried out in the presence of a suitable nucleophilic base. Suitable bases are alkali metal hydrides, such as sodium hydride, or alkali or alkaline earth carbonates, such as $Na_2CO_3$ or $K_2CO_3$, or alkali alcoholates, such as $(CH_3)_3CO^{\ominus}K^{\oplus}$, $NaOCH_3$ inter alia. The base is advantageously used in at least an equimolar amount based on the starting materials.

The cycloaddition reaction is advantageously carried out in an inert solvent. The following, preferably anhydrous, solvents are suitable: aromatic and aliphatic hydrocarbons, such as benzene, toluene, xylenes, petroleum ether, ligroin, cyclohexane; ethers and ethereal compounds, such as dialkyl ethers (diethyl ether, diisopropyl ether, t-butylmethyl ether etc.), dimethoxymethane, dioxane, tetrahydrofuran, anisole; alcohols, such as methanol or ethanol; sulfones, such as dimethyl sulfoxide; dimethylformamide; and mixtures of such solvents.

The cycloaddition is generally carried out at temperature of from −30° to +120° C., preferably at from −30° to +50° C. or at the boiling point of the solvent or solvent mixture.

By selecting suitable bases, the cycloaddition can advantageously also be carried out in aqueous medium. Suitable bases in such cases are water-soluble inorganic and organic bases, especially alkali hydroxides, such as LiOH, NaOH or KOH, and ammonium bases, for example tetraalkylammonium hydroxides, such as $(CH_3)_4NOH$. The base is used in at least an equimolar amount based on the starting materials. When using aqueous bases, the reaction is advantageously performed in a heterogeneous two-phase system.

Examples of suitable solvents for the organic water-immiscible phase are as follows: aliphatic and aromatic hydrocarbons, such as pentane, hexane, cyclohexane, petroleum ether, ligroin, benzene, toluene, xylenes etc., halogenated hydrocarbons, such as dichloromethane, chloroform, carbon tetrachloride, ethylene dichloride, 1,2-dichloroethane, tetrachloroethylene etc., or aliphatic ethers, such as diethyl ether, diisopropyl ether, t-butylmethyl ether etc.

In this method of carrying out the process the presence of a phase transfer catalyst can be of advantage in accelerating the reaction rate. Examples of such catalysts are tetraalkylammonium halides, hydrogen sulfates or hydroxides, such as tetrabutylammonium chloride, bromide or iodide; triethylbenzylammonium chloride or bromide; tetrapropylammonium chloride, bromide or iodide, etc. Phosphonium salts are also suitable phase transfer catalysts.

The phase transfer-catalysed cycloaddition can be carried out at temperatures of from 0° to 80° C., preferably from 10° to 50° C. or at the boiling point of the solvent mixture.

The cycloaddition in the described methods of execution can be carried out under normal pressure; the duration of the reaction is generally from 1 to 16 hours, and in the case of phase transfer catalysis from 0.5 to 10 hours.

Reaction step b)

The acylation of compound Ia is carried out under conventional conditions known to the person skilled in the art.

Examples of suitable solvents or diluents are aliphatic and aromatic hydrocarbons, such as benzene, toluene, xylenes or petroleum ether; halogenated hydrocarbons, such as chlorobenzene, methylene chloride, ethylene chloride, chloroform, carbon tetrachloride or tetrachloroethylene; ethers and ethereal compounds, such as dialkyl ethers (diethyl ether, diisopropyl ether, tert.-butylmethyl ether etc.), dioxane or tetrahydrofuran; nitriles, such as acetonitrile or propionitrile; ketones, such as acetone, diethyl ketone or methyl ethyl ketone; and mixtures of such solvents. Tetrahydrofuran and dioxane are preferred.

Suitable acid-binding agents are inorganic bases, for example oxides, hydroxides, carbonates or hydrogen carbonates of alkali metals or alkaline earth metals and also alkali hydrides or alkali acetates, as well as organic bases, for example tertiary amines, such as trialkylamines (trimethylamine, triethylamine etc.), pyridine or pyridine bases (4-dimethylaminopyridine, 4-pyrrolidylaminopyridine). Trialkylamines, such as trimethylamine or triethylamine, are preferred.

The reaction temperature is variable depending on the reaction conditions. It is generally from −25° C. to 100° C., preferably from −10° to 75° C.

Reaction step c)

Suitable reactive sulfenic acid derivatives for the sulfenylation reaction are, for example, the lower alkyl esters and preferably the sulfonic acid halides, especially the chlorides and bromides, more especially the chlorides. Lower alkyl here denotes $C_1$–$C_6$alkyl.

Both organic and inorganic bases can be used successfully as bases. Suitable inorganic bases are, for example, alkali and alkaline earth carbonates, such as sodium carbonate, potassium carbonate, calcium carbonate etc. Suitable organic bases are, for example, tertiary amines, such as trialkylamines (triethylamine, methyldiethylamine), N,N-dimethoxycyclohexylamine, N-methylpiperidine, N,N-dimethylaniline or pyridines. Trialkylamines are preferred. Advantageously a stoichiometric amount or an excess, for example up to 100% excess, of base is used in relation to the pyrrole Ia. The reactive derivative of the sulfenic acid IV is also added either in stoichiometric amount or in excess.

The sulfenylation reaction can be carried out in the presence or absence, but preferably in the presence, of an inert solvent or solvent mixture. In principle, customary organic solvents are suitable for this reaction provided they do not contain any reactive hydrogen atoms. The following, for example, are suitable: aliphatic and aromatic hydrocarbons, such as benzene, toluene, xylenes or petroleum ether; halogenated hydrocarbons, such as chlorobenzene, methylene chloride, ethylene chloride, chloroform, carbon tetrachloride or tetrachloroethylene; ethers and ethereal compounds, such as dialkyl ethers (diethyl ether, diisopropyl ether, tert.-butyl methyl ether etc.), ethylene glycol and diethylene glycol diethers and monoethers having from 1 to 4 carbon atoms in each of the alkyl moieties, such as ethylene glycol dimethyl, diethyl and di-n-butyl ether, diethylene glycol diethyl and di-n-butyl ether, ethylene glycol monomethyl ether and diethylene glycol monomethyl ether; furan, dimethoxyethane, dioxane, tetrahydrofuran, anisole; sulfones, such as dimethyl sulfoxide; ketones, such as acetone or methyl ethyl ketone; esters, such as ethyl acetate, propyl acetate or butyl acetate; and mixtures of such solvents. In some cases the sulfenylation reagent of formula IV can itself also act as solvent.

In order to increase the reaction rate, it is possible for a reaction catalyst, such as 4-dimethylaminopyridine, to be added.

The sulfenylation reaction is generally carried out at temperatures of from −30° to +100° C., preferably from −10° to +20° C. According to experience the reaction times are approximately from 0.5 to 20 h at such temperatures. By adding a reaction catalyst it is possible to reduce the reaction time to less than 0.5 h.

Reaction step d)

The reaction of the compound of formula Ia with an aldehyde of formula V can be carried out in the presence or absence of inert solvents or solvent mixtures. Examples of suitable solvents are aromatic hydrocarbons, such as benzene, toluene or xylenes; halogenated hydrocarbons, such as chlorobenzene; aliphatic hydrocarbons, such as petroleum ether; ethers and ethereal compounds, such as dialkyl ethers (diethyl ether, diisopropyl ether, tert.-butylmethyl ether etc.), furan, dimethoxyethane, dioxane, tetrahydrofuran; dimethylformamide etc.

The reaction of compounds of formula Ia with compounds of formula V is advantageously carried out without solvents but with an excess amount of the aldehyde of formula V. Depending on the nature of the aldehyde, the reaction is carried out in solution or in the molten state. The addition of acidic or basic catalysts has a favourable effect on the reaction rate. Suitable acid catalysts are, for example, anhydrous hydrogen halides and mineral acids, such as HCl, HBr or $H_2SO_4$, and also concentrated hydrochloric acid. As basic catalysts it is possible to use, for example, trialkylamines (trimethylamine, triethylamine, dimethylethylamine etc.), alkali and alkaline earth carbonates (such as $Na_2CO_3$, $BaCO_3$, $MgCO_3$, $K_2CO_3$ etc.) or alkali alcoholates (such as $NaOCH_3$, $NaOC_2H_5$, $KO(iso-C_3H_7)$, $KO(t$-butyl). The temperatures for this reaction are generally from 0° to 200° C., preferably from 0° to 160° C., and the reaction time is from 1 to 24 hours, especially from 1 to 4 hours.

The exchange of the free hydroxy group in the compounds of formula Ic for a group Y is preferably carried out in an inert solvent. Examples of such solvents are: aromatic and aliphatic hydrocarbons, such as benzene, toluene, xylenes, petroleum ether, ligroin or cyclohexane; halogenated hydrocarbons, such as chlorobenzene, methylene chloride, ethylene chloride, chloroform, carbon tetrachloride or tetrachloroethylene; ethers and ethereal compounds, such as diethyl ether, diisopropyl ether, t-butylmethyl ether, dimethoxyethane, dioxane, tetrahydrofuran or anisole; esters, such as ethyl acetate, propyl acetate or butyl acetate; nitriles, such as acetonitrile; or compounds such as dimethyl sulfoxide and dimethylformamide; and mixtures of such solvents.

The group Y is introduced according to conventional methods. If Y is chlorine, then, for example, phosphorus oxychloride, phosphorus trichloride, phosphorus pentachloride or, preferably, thionyl chloride, is used as reagent. The reaction is generally carried out at temperatures of from 0° to 120° C. If Y is bromine, then preferably phosphorus tribromide or phosphorus pentabromide is used and the reaction is carried out at 0° to 50° C. If Y is the group $-O-C(O)-R_4$, then the corresponding acid halide, especially the corresponding acid chloride, is usually used as reagent. In that case it is advantageous for the reaction to be carried out at temperatures of from $-20°$ to $+50°$ C., preferably from $-10°$ to $+30°$ C., in the presence of a weak base, such as pyridine or triethylamine. In addition, 4-dialkylaminopyridines, such as 4-dimethyl-or 4-diethylaminopyridine, may be added as catalysts in order to accelerate the reaction.

The reaction of compounds of formula Ie with salts of formula VII is usually carried out in the presence of a customary inert solvent or solvent mixture. Examples of such solvents are: aromatic and aliphatic hydrocarbons, such as benzene, toluene, xylenes, petroleum ether, ligroin or cyclohexane; ethers and ethereal compounds, such as dialkyl ethers, for example diethyl ether, diisopropyl ether, t-butylmethyl ether, dimethoxyethane, dioxane, tetrahydrofuran or anisole; esters, such as ethyl acetate, propyl acetate or butyl acetate; nitriles, such as acetonitrile; or compounds such as dimethyl sulfoxide and dimethylformamide; and mixtures of such solvents.

The addition of catalytic amounts of a crown ether, such as, for example, 18-crown-6 or 15-crown-5 have a favourable effect on the course of this reaction. The reaction temperatures are generally from 0° to 150° C., preferably from 20° to 80° C. The reaction time is from 1 to 24 hours.

In a preferred embodiment, the preparation of compounds of formula Id, especially those in which $R_3=CCl_3$ or $R_3=H$, starting from compounds of formula Ia, is advantageously carried out in a so-called one-pot process. Advantageously, one of the above-mentioned inert solvents or diluents is used for this process, an ethereal compound for example, such as tetrahydrofuran, being especially suitable, and the process is carried out in the presence of a weak base, such as a trialkylamine (triethylamine) or pyridine. Chloral or paraformaldehyde is used as reagent. The reaction can be accelerated by the addition of a catalyst, such as, for example, 1,8-diazabicyclo[5.4.0]undec-7-ene [DBU]. The temperatures in this first reaction step are from $-20°$ to $+100°$ C., preferably from 0° to 50° C., and the reaction time is from 0.5 to 2 hours. A hydroxy derivative of formula Ic is formed as intermediate which is not isolated but is reacted in the same reaction solution with a compound of formula VI at from $-30°$ to $+30°$ C., preferably from $-10°$ to 0° C. and in the presence of catalytic amounts of a 4-dialkylaminopyridine, preferably 4-dimethylaminopyridine. The reaction time for this second step is from 0.5 to 16 hours.

The starting materials of formula V, VI and VII are generally known, or can be prepared according to methods known per se.

Reaction step e)

The reaction of the compound of formula Ia with a compound of formula VIII is preferably carried out in a suitable inert solvent. Suitable protic solvents are, for example: water, alcohols (especially alkanols, such as methanol, ethanol, isopropanol, n-propanol etc.) or carboxylic acids (especially alkanecarboxylic acids, such as formic acid, acetic acid, propionic acid etc.). If the reaction step is carried out in a protic solvent, then, for example, the following substances can be used as reaction catalysts: organic bases, such as, for example, 1,8-diazabicyclo[5.4.0]undec-7-ene, tertiary amines, such as trialkylamines (trimethylamine, triethylamine, dimethylethylamine etc.), triethylenediamine, piperidine, pyridine, 4-dimethylaminopyridine, 4-pyrrolidylpyridine etc., or inorganic bases, such as the oxides, hydroxides, hydrides, carbonates, hydrogen carbonates and alcoholates of alkali metals or alkaline earth metals (for example $Na_2CO_3$, $BaCO_3$, $MgCO_3$, $K_2CO_3$, $CaHCO_3$, $NaOCH_3$, $NaOC_2H_5$, $KO(iso-C_3H_7)$, $KO(t-butyl)$, NaH, CaO etc.); organic acids, such as, for example, carboxylic acids (acetic acid, formic acid, propionic acid etc.) aliphatic and aromatic sulfonic acids, such as methanesulfonic acid, ethanesulfonic acid, toluenesulfonic acid or benzenesulfonic acid, etc.; or inorganic acids, such as mineral acids, for example phosphoric acid, sulfuric acid, nitric acid or hydrohalic acids (hydrochloric acid, hydrobromic acid, hydriodic acid or hydrofluoric acid). In this reaction variant, acids or bases are advantageously added in catalytic amounts. Generally, an excess of the amine of formula VIII is sufficient. The formaldehyde in this variant is preferably used in the form of its aqueous solution (formalin) or as a trimer (1,3,5-trioxane) or as a polymer (paraformaldehyde).

Suitable aprotic solvents are, for example, aliphatic or aromatic hydrocarbons, such as benzene, toluene, xylenes, petroleum ether, ligroin, benzines or cyclohexane; ethers and ethereal compounds, such as diethyl ether, diisopropyl ether, tert.-butylmethyl ether, dimethoxyethane, tetrahydrofuran, dioxane or anisole; esters, such as ethyl acetate, propyl acetate or butyl acetate; or compounds such as dimethylformamide and dimethyl sulfoxide; and mixtures of such solvents. The catalyst used are, for example, the above-listed bases. In this reaction step the formaldehyde is preferably used in the form of 1,3,5-trioxane or paraformaldehyde.

The sulfenic acids of formula IV and the amines of formula VIII are known or can be prepared according to methods known per se.

For the preparation of the cyanoacrylic acid, its esters or amides of formula IIa, an aldehyde of formula IX is used as starting material and is condensed in the conventional manner known to the person skilled in the art with cyanoacetic acid, cyanoacetic acid ester or cyanoacetic acid amide [Org. React. 15, 204–599 (1967)].

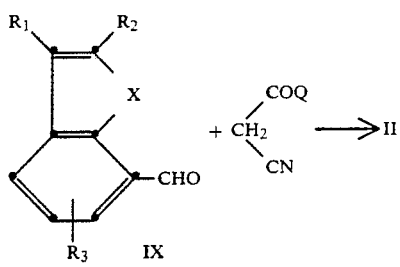

The 7-benzofuran-carbaldehydes of formula IXa

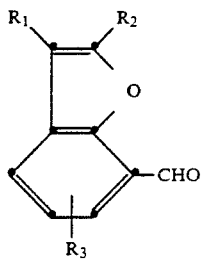

are in some cases known [J. Chem. Perk. Transl. 2(a) 1479–1485, Tetrahedron Letters (24), 45, 5023–5024 (1983)] and can generally be prepared analogously to the methods published therein.

The novel 7-benzothiophene-carbaldehydes of formula IXb

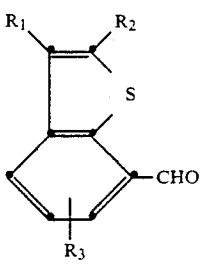

can be prepared analogously to the afore-mentioned methods that result in 7-benzofurancarbaldehydes. The 7-halomethylbenzothiophenes of formula XV obtainable by halogenation of the 7-methylbenzothiophenes of formula X are reacted either with hexamethylenetetramine (Sommelet reaction) or with a nitroalkane and with an alkali alcoholate:

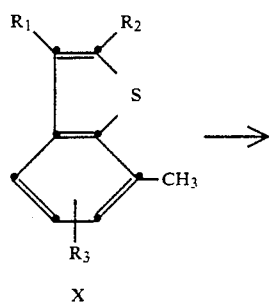

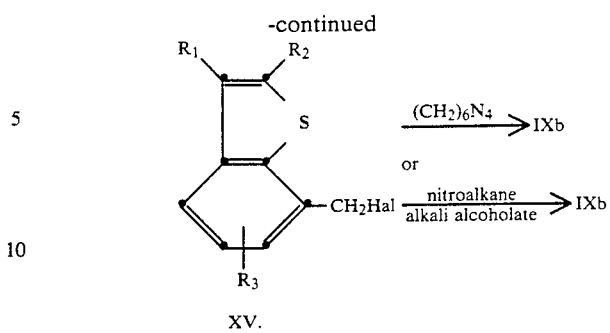

In the bromination of X using a large excess of N-bromosuccinimide, the 3-bromo-7-bromomethylbenzothiophene is obtainable directly, and can in turn be converted into the 7-bromomethylbenzothiophene by reaction with 1 mole of hydrogen in the presence of Pd-catalyst.

7-Methylbenzofurans and 7-methylbenzothiophenes are known from DE-OS 3,302,814, from Bull. Soc. Chim. Fr. 1962; 30–34 and from Bull. Soc. Chim. Fr. 1961; 2410–2417.

The preparation of compounds of formula X can generally be carried out according to the methods described in those references.

The novel cyanoacrylic acid derivatives of formula IIa are valuable intermediates for the preparation of the microbicidal compounds of formula I and the present application also extends to them.

The preparation of the acrylonitriles of formula IIb uses as starting materials the 7-aminobenzofurans of formula XIa or 7-aminobenzothiophenes of formula XIb obtainable by reduction of the corresponding nitro compounds, the starting materials being reacted in the conventional manner known to the person skilled in the art to form the diazonium salt of formula XII:

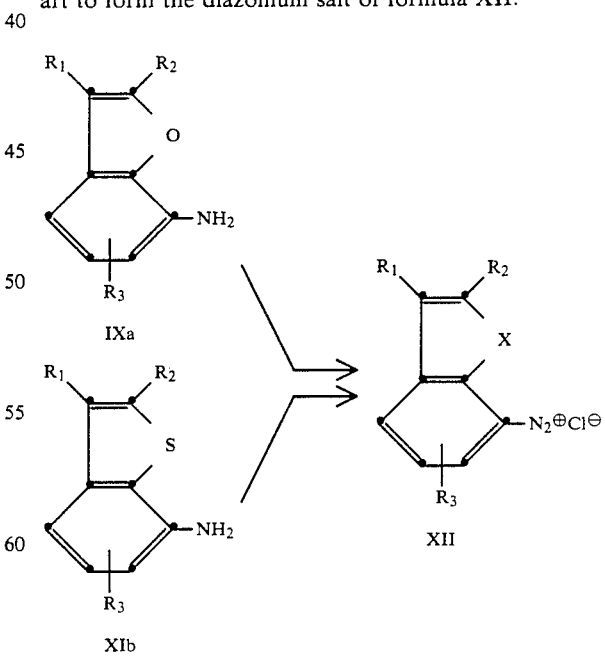

The diazonium salt of formula XII is then reacted with the acrylonitrile of formula XIII in the presence of Cu(I) chloride in an aqueous reaction medium, with a dialkyl ketone as solubiliser, to form the addition product of formula XIV:

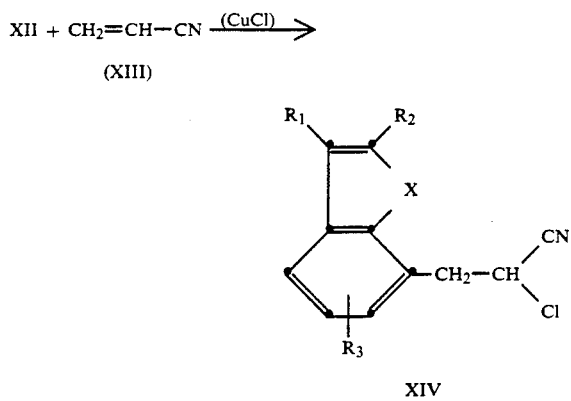

XIV

Subsequently, by reacting the compound of formula XIV with an acid-binding agent in an inert organic solvent, HCl is removed and an acrylic acid nitrile (formula IIb) is obtained, the product being a cis/trans isomeric mixture which can be separated in conventional manner by chromatography:

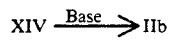

The reaction performed between the diazonium salt (formula XII) and the acrylonitrile (formula XIII) is a modification of the normal "Sandmeyer" method effected by applying the conditions of the "Meerwein" reaction of aromatic diazonium compounds to α,β-unsaturated carbonyl compounds, as a result of which the replacement of the diazonium group by halogen is suppressed in favour of the addition reaction (cf. E. Müller, Angew. Chemie 61, 178–183, 1949).

In carrying out the reaction in practice, the diazonium salt and acrylonitrile reactants are used in a ratio of from 1:1 to 1:8, preferably 1:2. The reaction temperatures are from 20° to 50° C., preferably from 25° to 35° C. The reaction time is from 0.5 to 10 hours, preferably from 1 to 3 hours. The solubiliser used in the aqueous reaction medium is preferably ethyl methyl ketone.

Examples of the inert solvents used in the removal of HCl from the compound of formula XIV are aliphatic and aromatic hydrocarbons, such as benzene, toluene, xylenes or petroleum ether; halogenated hydrocarbons, such as chlorobenzene, methylene chloride, ethylene chloride, chloroform, carbon tetrachloride or tetrachloroethylene; ethers and ethereal compounds, such as dialkyl ethers (diethyl ether, diisopropyl ether, tert.-butylmethyl ether etc.), dioxane or tetrahydrofuran; nitriles, such as acetonitrile or propionitrile; N,N-dialkylated amides, such as dimethylformamide; dimethyl sulfoxide; ketones, such as acetone, diethyl ketone or methyl ethyl ketone; and mixtures of such solvents. Weakly nucleophilic organic bases, preferably trialkylamines, are used as acid-binding agents. The removal reaction is carried out at temperatures that range from room temperature to the reflux temperature of the solvent used, preferably from 30° to 60° C. The reaction time is from 1 to 24 hours, preferably from 3 to 12 hours.

The compound of formula IIb is a valuable intermediate for the preparation of fungicides and as a novel compound forms part of the invention.

Some of the mentioned 7-nitrobenzofurans and 7-nitrobenzothiophenes of the formula

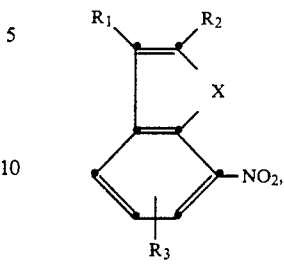

in which $R_1$, $R_2$, $R_3$ and X have the meanings given in the definition of compounds of formula I, which can be converted by reduction into the amines of formulae XIa and XIb, are described in J. Med. Chem. 13, (6) 1102–5 (1970) and in Ann. Chim. (Roma) 47885–91 (1957). The nitro compounds serving as precursors to the compounds of formulae XIa and XIb can generally be prepared analogously to the methods described therein.

N-benzothienylmethyl-N-alkenylalkylamines are known as human antimycotics from DE-OS 3,302,814. The compounds are not, however, benzothiophenes that are bonded to a substituted or an unsubstituted pyrrole radical.

The preparation of benzofuran derivatives is described in Japanese Patent Application J5-9104-374A (CA 101 191676m, 1984). The resulting compounds are suitable as intermediates for agrochemicals. No benzofurans that are bonded to a substituted or an unsubstituted pyrrole radical are, however, mentioned therein.

Benzofuran- and benzothiophene-7-carboxylic acid derivatives having the property of inhibiting reflective contraction of urinary bladder are described in EP-A 270342.

Benzothiophenes and benzofurans bonded to a pyrrole radical that have microbicidal or fungicidal activity are not known. The benzothiophene and benzofuran derivatives of formula I according to the invention are novel.

Surprisingly, it has now been found that the compounds of formula I of the invention have a very advantageous biocidal spectrum of activity against destructive microorganisms, especially against phytopathogenic fungi and bacteria, that is very satisfactory for practical requirements. They have very advantageous curative, systemic and, in particular, preventive properties, and can be used for protecting numerous cultivated plants. With the compounds of formula I it is possible to inhibit or destroy the pests that occur on plants or parts of plants (fruit, blossoms, leaves, stems, tubers, roots) in different crops of useful plants, while at the same time the parts of the plants that grow later are also protected from attack by phytopathogenic microorganisms.

The compounds of the invention are effective, for example, against the phytopathogenic fungi belonging to the following classes: Ascomycetes, for example Erysiphe, Sclerotinia, Fusarium, Monilinia and Helminthosporium; Basidiomycetes, such as, for example, Puccinia, Tilletia and Rhizoctonia; and the Oomycetes belonging to the class of the Phycomycetes, such as Phytophthora. As plant protective compositions, the compounds of formula I can be used particularly successfully against important harmful fungi from the family of Fungi imperfecti, for example against Cercospora, Pyricularia and especially against Botrytis. With grey mould rot on vines, strawberries, apples, onion and other varieties of fruit and vegetables, Botrytis spp. (*B. cinerea*, *B. allii*) represent an economically significant damage factor. In particular compounds 1.1, 1.2 and 1.8 from Table 1 exhibit a broad spectrum of activity in this respect. They not only have an excellent fungicidal activity against Pyricularia, Botrytis and Rhizoctonia but are also suitable for the successful control of Erysiphe and Venturia species. In addition, the compounds have a systemic action. Furthermore, the compounds of formula I can be used successfully for the protection of perishable goods of vegetable or animal origin. They control mould fungi, such as Penicillium, Aspergillus, Rhizopus, Fusarium, Helminthosporium, Nigrospora and Alternaria, and also bacteria, such as butyric acid bacteria, and yeasts, such as Candida. These active substances furthermore exhibit outstanding activity against soil-borne and seed-borne fungi.

As plant-protective agents, the compounds of formula I have, for practical field application purposes, a very favourable spectrum of activity for the protection of crops without having a disadvantageous effect on the crops as a result of undesired side-effects.

Target crops to be protected within the scope of this invention comprise, for example, the following species of plants: cereals (wheat, barley, rye, oats, rice, sorghum and related crops); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (cucumber, marrows, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor), or plants such as maize, tobacco, nuts, coffee, sugar cane, tea, vines, hops, bananas and natural rubber plants, as well as ornamentals (Compositae).

The compounds of formula I can furthermore also be used as dressing agents for protecting seeds (fruit, tubers, grains) and plant cuttings against fungus infections as well as against phytopathogenic fungi that occur in the soil; they are distinguished in particular as cereal dressing agents in the control of fungal organisms such as, for example, species of Fusarium, Helminthosporium and Tilletia.

The invention thus also relates to microbicidal compositions and to the use of the compounds of formula I for controlling phytopathogenic microorganisms, especially plant-destructive fungi, or for protecting plants and stored goods of vegetable or animal origin from attack by said microorganisms.

Within the scope of the present invention the term "stored goods" shall be understood as meaning natural vegetable and/or animal materials and processed products thereof, for example the plants, listed in the following, which have been removed from their natural life cycle, and their plant parts (stems, leaves, tubers, seeds, fruit, grains), which are in freshly harvested condition or in a processed form (pre-dried, moistened, comminuted, ground, roasted). The following agricultural products may be mentioned as examples which are not of a limiting nature to the field of application within the scope of this invention: cereals (such as wheat, barley, rye, oats, rice, sorghum and related crops); beet (such as carrots, sugar beet and fodder beet); pomes, drupes and soft fruit (such as apples, pears, plums, peaches, almonds, cherries, strawberries, raspberries and blackberries); leguminous plants (such as beans, lentils, peas, soybeans); oil plants (such as rape, mustard, poppy, olives, sunflowers, coconut, castor oil plants, cocoa beans, groundnuts); cucumber plants (such as cucumber, marrows, melons); fiber plants (such as cotton, flax, hemp, jute, nettles); citrus fruit; vegetables (such as spinach, lettuce, asparagus, cabbages, onions, tomatoes, potatoes, paprika); lauraceae (such as avocados, cinnamon, camphor), or maize, tobacco, nuts, coffee, sugar cane, tea, vines, chestnuts, hops, bananas, grass and hay.

Examples of natural products of animal origin are especially dried processed meat and fish products, such as dried meat, dried fish, meat concentrates, bonemeal, fishmeal and dried animal feed.

The treated stored goods are given lasting protection against attack by mould fungi and other undesired microorganisms by treatment with compounds of formula I. As a result, the formation of toxic and in some cases carcinogenic mould fungi (aflatoxins and ochratoxins) is prevented, the goods are protected from rotting and the quality is maintained for a prolonged period. The method according to the invention can be applied to all dry and moist stored goods that are susceptible to attack by microorganisms, such as yeasts, bacteria and especially mould fungi.

A preferred method of applying the active ingredient comprises spraying or wetting the substrate with a liquid preparation or mixing the substrate with a solid preparation of the active ingredient. The described preservation method also forms part of the present invention.

Compounds of formula I are usually used in the form of compositions and can be applied to the area, plant or substrate to be treated, simultaneously or in succession, with other active ingredients. These other active ingredients can be fertilizers or micronutrient donors or other preparations that influence plant growth. They can, however, also be selective herbicides, insecticides, fungicides, bactericides, nematicides, molluscicides or mixtures of several of these preparations, if desired together with further carriers, surfactants or other application-promoting adjuvants customarily employed in the art of formulation.

Suitable carriers and additives can be solid or liquid and correspond to the substances ordinarily employed in formulation technology, e.g. natural or regenerated mineral substances, solvents, dispersants, wetting agents, tackifiers, thickeners, binders or fertilisers. Particularly advantageous adjuvants are phospholipids.

A preferred method of applying a compound of formula I, or an (agro)-chemical composition that contains at least one of said compounds, is application to the leaves (foliar application). The number of applications and the rate of application depend on the risk of infestation by the corresponding pathogen (species of fungus). However, the compounds of formula I can also penetrate the plant through the roots via the soil (systemic action) if the locus of the plant is impregnated with a liquid formulation, or if the compounds are applied in solid form to the soil, e.g. in granular form (soil application). The compounds of formula I may, however, also be applied to seeds (coating) either by impregnating the seeds with a liquid formulation of the active ingredient, or coating them with a solid formulation. In special cases, further types of application are also possible, e.g. selective treatment of the plant stems or buds.

The compounds of formula I are used in unmodified form or, preferably, together with the adjuvants conventionally employed in the art of formulation, and are therefore formulated in known manner e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 20 g to 5 kg of active ingredient (a.i.) per hectare, preferably from 100 g to 2 kg a.i./ha, most preferably from 200 g to 600 g a.i./ha.

In the preparation of dressed seeds, the ratio of seeds:-compound of formula I is so selected that the rate of application after sowing is from 0.1 g a.i./ha to 500 g a.i./ha, preferably from 0.5 g a.i./ha to 100 g a.i./ha, that is to say the indicated amount of active ingredient is to be found together with the seeds on 1 ha of cultivated area after sowing.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexane, strongly polar solvents such as N-methyl-2-pyrrolidone, dimethyl sulfoxide or dimethylformamide, as well as vegetable oils or epoxidised vegetable oils, such as epoxidised coconut oil, sunflower oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues, such as, for example, cork dust or sawdust.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Mention may also be made of fatty acid methyllaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyldi(2-chloroethyl)ethylammonium bromide. In the field of protection of stored goods, additives that are safe for human and animal food are preferred.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries, such as stabilisers, antifoams, viscosity regulators, binders, tackifiers as well as fertilisers or other active ingredients for obtaining special effects.

The present invention relates to such (agro)chemical compositions.

The following Examples serve to illustrate the invention without implying any limitation of the scope thereof (percentages and parts are by weight; temperatures are in degrees Celsius).

1. PREPARATION EXAMPLES

P.1 Preparation of 3-bromo-7-bromomethylbenzothiophene 0.2 g each of dibenzoyl peroxide and α,α-azoisobutyronitrile and 210 g (1.14 mole) of N-bromosuccinimide are added in several portions to a solution of 77.1 g (0.52 mole) of 7-methylbenzothiophene in 400 ml of CCl$_4$ at 80° C., and the reaction mixture is boiled under reflux for 12 hours. The reaction mixture is then cooled to room temperature and filtered, the solvent of the filtrate is evaporated in vacuo, the residue is dissolved in a mixture of hexane:ethyl acetate 4:1 and after purification by chromatography on silica gel the solvent is evaporated in vacuo. 142 g (89% of the theoretical amount) of the target product are isolated as residue.

P.2 Preparation of 3-bromo-7-benzothiophene-carbaldehyde

With stirring, 68.2 g (0.74 mole) of 2-nitropropane are added dropwise at room temperature, over a period of 45 minutes, to a Na-ethoxide solution prepared under an argon atmosphere from 14.2 g (0.61 mole) of sodium and 800 ml of abs. ethanol. 137 g (0.61 mole) of 3-bromo-7-bromomethylbenzothiophene are then added dropwise at room temperature, over a period of 1.5 hours, to the resulting white suspension. After the reaction mixture has been stirred for one day, the solvent is evaporated off from the reaction mixture in vacuo, the resulting residue of 101.2 g is dissolved in a mixture of hexane:diethyl ether 1:1 and the solution is purified by chromatography on silica gel. After evaporation of the solvent, 81 g (80% of the theoretical amount) of 3-bromo-7-benzothiophene-carbaldehyde are obtained as residue.

P.3 Preparation of 7-benzothiophene-carbaldehyde 2 g of 5% palladium-on carbon catalyst are added to a solution of 10.4 g (43.15 mmoles) of 3-bromo-7-benzothiophene-carbaldehyde in 130 ml of tetrahydrofuran and 5.6 ml of triethylamine and the mixture is hydrogenated with hydrogen in a hydrogenating apparatus for 45 hours at 20°-22° C. under atmospheric pressure. The catalyst is then filtered off and the solvent is evaporated in vacuo from the filtrate. The residue is dissolved with 50 ml each of water and ethyl acetate, and 5.2 g (67.5% of the theoretical amount) of 7-benzothiophene-carbaldehyde are obtainable as residue from the separated organic phase after evaporation of the solvent in vacuo.

P.4 Preparation of 2-cyano-3-(benzothiophen-7-yl)-acrylic acid methyl ester

A mixture of 1.0 g (6.2 mmoles) of 7-benzothiophene-carbaldehyde, 0.4 g (6.8 mmoles) of cyanoacetic acid methyl ester, 0.07 g of ammonium acetate, 0.2 g of acetic acid, 1 g of molecular sieve (3 Å) and 10 ml of toluene are boiled under reflux for 4 hours, and then the reaction mixture is cooled and mixed with 20 ml of ethyl acetate and with 20 ml of 10% NaCl solution. The separated organic phase is dried with MgSO$_4$, filtered and the solvent is evaporated in vacuo. 1.5 g of 2-cyano-3-(benzothiophen-7-yl)-acrylic acid methyl ester in the form of a crude product is obtained as residue.

P.5 Preparation of 2-cyano-3-(bromobenzothiophen-7-yl)-acrylic acid methyl ester 1.2 g of 3-bromo-7-benzothiophene-carbaldehyde is reacted with cyanoacetic acid methyl ester analogously to Example P. 4 to form 2-cyano-3-(bromobenzothiophen-7-yl)-acrylic acid methyl ester.

P.6 Preparation of 3-(benzothiophen-7-yl)-4-cyanopyrrole (Compound No. 1)

At 5° C., a solution of 2 g (10.8 mmoles) of Na-methoxide dissolved in 5 ml of methanol is added to a mixture having a temperature of 5° C. of 2.2 g (9.05 mmoles) of 2-cyano-3-(benzothiophen-7-yl)acrylic acid methyl ester and 1.8 g (9.05 mmoles) of p-toluenesulfonylmethyl isocyanide ("Tosmic") in 13 ml of methanol. After the reaction mixture has been stirred for two hours at room temperature, a further 2 g of Na-methoxide dissolved in 5 ml of methanol are added. The reaction mixture is then poured onto 200 ml of water and stirred for 30 minutes. The product obtained in the form of a suspension is filtered off and dissolved in 20 ml of ethyl acetate. The mother liquor is extracted with 20 ml of ethyl acetate, the combined ethyl acetate solutions are washed with saturated NaCl solution until neutral and dried over MgSO$_4$, and the solvent is evaporated in vacuo. The crude product obtained as residue weighs 1.8 g (90% of the theoretical amount). The product, dissolved in a mixture of hexane:ethyl acetate 2:1, is purified by chromatography on silica gel. Evaporation of the solvent yields 1.4 g (70% of the theoretical amount) of its 2-cyano-3-(-bromobenzothiophen-7-yl)-acrylic acid methyl ester. M.p.: 138°–139° C.

P.7 Preparation of 3-(3-bromobenzothiophen-7-yl)-4-cyanopyrrole (Compound No. 2)

19 g (59 mmoles) of 2-cyano-3-(bromobenzothiophen-7-yl)-acrylic acid methyl ester are reacted with "Tosmic" analogously to Example P. 6 to form 3-(3-bromobenzothiophen-7-yl)-4-cyanopyrrole having a melting point of 130°–134° C. Pure yield 83% of the theoretical amount.

Table 1 contains the compounds that can be prepared in an analogous manner, and also derivatives thereof that can be prepared in accordance with the preceding description.

TABLE 1

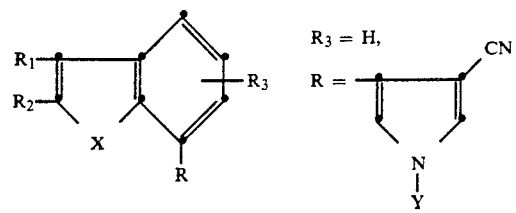

R₃ = H,  R = (structure with CN, N-Y)

| Comp. No. | X | R₁ | R₂ | Y | Physical constants |
|---|---|---|---|---|---|
| 1 | S | H | H | H | m.p. = 138–139° C. |
| 2 | S | Br | H | H | m.p. = 130–134° C. |
| 3 | S | H | CF₃ | H | |
| 4 | S | H | CH₃ | H | |
| 5 | S | CH₂Br | H | H | |
| 6 | O | H | CH₃ | H | m.p. = 141–144° C. |
| 7 | O | CH₂Br | H | H | |
| 8 | O | H | H | H | m.p. = 148–149° C. |
| 9 | O | Br | H | H | |
| 10 | S | H | H | CHO | |
| 11 | S | H | H | COCH₃ | |
| 12 | S | CH₃ | H | COCH₂CH₃ | |
| 13 | S | H | H | SCCl₂F | |
| 14 | S | Br | H | COCH₃ | |
| 15 | O | H | H | CHO | |
| 16 | O | CH₃ | H | COCH₂CH₃ | |
| 17 | O | H | H | SCCl₂F | |
| 18 | O | Br | H | COCH₃ | |

2. FORMULATION EXAMPLES

| 2.1. Emulsifiable concentrates | a) | b) | c) |
|---|---|---|---|
| a compound of Table 1 | 25% | 40% | 50% |
| calcium dodecylbenzenesulfonate | 5% | 8% | 6% |
| castor oil polyethylene glycol ether (36 moles of ethylene oxide) | 5% | — | — |
| tributylphenol polyethylene glycol ether (30 moles of ethylene oxide) | — | 12% | 4% |
| cyclohexanone | — | 15% | 20% |
| xylene mixture | 65% | 25% | 20% |

Emulsions of any desired concentration can be produced from such concentrates by dilution with water.

| 2.2. Solutions | a) | b) | c) | d) |
|---|---|---|---|---|
| a compound of Table 1 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum fraction (boiling range 160–190° C.) | — | — | 94% | — |

| 2.3. Granulates | a) | b) |
|---|---|---|
| a compound of Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| 2.4. Dusts | a) | b) |
|---|---|---|
| a compound of Table 1 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| 2.5. Wettable powders | a) | b) | c) |
|---|---|---|---|
| a compound of Table 1 | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is ground in a suitable mill, affording wettable powders which can be diluted with water to give suspensions of the desired concentration.

| 2.6. Emulsifiable concentrate | |
|---|---|
| a compound of Table 1 | 10% |
| octylphenol polyethylene glycol ether (4–5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 2.7. Dusts | a) | b) |
|---|---|---|
| a compound of Table 1 | 5% | 8% |
| talcum | 95% | — |
| kaolin | — | 92% |

Ready-for-use dusts are obtained by mixing the active ingredient with the carrier and grinding the mixture in a suitable mill.

| 2.8. Extruder granulate | |
|---|---|
| a compound of Table 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.9. Coated granulate | |
|---|---|
| a compound of Table 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.10. Suspension concentrate | |
| --- | --- |
| a compound of Table 1 | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. BIOLOGICAL EXAMPLES:

Example 3.1.: Action against *Puccinia graminis* on Wheat a) Residual Protective Action Wheat plants are sprayed, 6 days after sowing, with a spray mixture (0.02% active ingredient) prepared from a wettable powder formulation of the test compound. After 24 hours the treated plants are infected with a uredospore suspension of the fungus. The infected plants are incubated for 48 hours at 95-100% relative humidity and about 20° C. and then stood in a greenhouse at about 22° C. Evaluation of rust pustule development is made 12 days after infection.

b) Systemic Action

Wheat plants are watered 5 days after sowing with a spray mixture (0.006% active ingredient based on the volume of the soil) prepared from a wettable powder formulation of the test compound. After 48 hours the treated plants are infected with a uredospore suspension of the fungus. The infected plants are then incubated for 48 hours at 95-100% relative humidity and about 20° C. and stood in a greenhouse at about 22° C. Evaluation of rust pustule development is made 12 days after infection.

Compounds from Table 1 exhibited very good activity against Puccinia fungi. Puccinia attack was 100% on untreated and infected control plants. Inter alia, compounds 1, 2 and 8 confined Puccinia attack to 0-5%.

Example 3.2.: Action against *Cercospora arachidicola* on Groundnut Plants

Residual Protective Action

Groundnut plants 10-15 cm in height are sprayed with a spray mixture (0.006% active ingredient) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks occur. Evaluation of the fungicidal action is made 12 days after infection and is based on the number and size of the specks.

Compared with untreated and infected controls (number and size of the specks=100%), Cercospora attack on groundnut plants treated with compounds from Table 1 was substantially reduced. In these tests, compounds, 1, 2 and 8 inhibited the occurrence of specks almost completely.

Example 3.3.: Action against *Erysiphe graminis* on Barley a) Residual Protective Action Barley plants about 8 cm in height are sprayed with a spray mixture (0.02% active ingredient) prepared from a wettable powder formulation of the test compound. The treated plants are dusted with conidia of the fungus after 3 to 4 hours. The infected barley plants are stood in a greenhouse at about 22° C. and the fungus attack is evaluated after 10 days. Compounds 1 and 2 from Table 1 were very effective against Erysiphe attack on barley.

Example 3.4.: Residual Protective Action against *Venturia inaequalis* on Apple Shoots Apple cuttings with 10-20 cm long fresh shoots are sprayed with a spray mixture (0.06% active ingredient) prepared from a wettable powder formulation of the test compound. The treated plants are infected 24 hours later with a conidia suspension of the fungus. The plants are then incubated for 5 days at 90-100% relative humidity and stood in a greenhouse for a further 10 days at 20°-24° C. Scab infestation is evaluated 1-5 days after infection.

Compounds of Table 1 exhibited a good activity against Venturia on apple shoots. Compounds 1, 2 and 8 confined disease attack to less than 10%. Venturia attack was 100% on untreated and infected shoots.

Example 3.5.: Action against *Botrytis cinerea* on Beans

Residual Protective Action

Bean plants about 10 cm in height are sprayed with a spray mixture (0.02% active ingredient) prepared from a wettable powder formulation of the test compound. After 48 hours, the treated plants are infected with a conidia suspension of the fungus. The infected plants are incubated for 3 days at 95-100% relative humidity and 21° C. and then evaluated for fungus attack. In many cases compounds of Table 1 inhibited the fungus infection completely. At a concentration of 0.02%, for example compounds 1, 2 and 8 proved completely effective (no visible disease attack). Attack on untreated and infected bean plants was 100%.

Example 3.6.: Action against *Botrytis cinerea* on Apples

Artificially damaged apples are treated by applying drops of a spray mixture, prepared from a wettable powder formulation of the test compound, to the injury sites. The treated fruit is then inoculated with a spore suspension of *Botrytis cinerea* and incubated for 1 week at high humidity and about 20° C.

In the evaluation, the number of rotted injury sites is counted and from this the fungicidal activity of the test compound is derived. Compounds of Table 1 were very effective against Botrytis attack on apple fruits. Inter alia, compounds 1, 2 and 8 inhibited fungus attack almost completely (disease attack 0-5%) compared with untreated control fruits (100% attack).

What is claimed is:

1. A compound of formula IIa

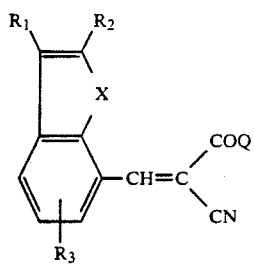

(IIa)

wherein X is oxygen or sulfur, $R_1$ is hydrogen, halogen, $C_1$–$C_4$alkyl or $C_1$–$C_4$haloalkyl, $R_2$ is hydrogen, halogen, $C_1$–$C_4$alkyl or $C_1$–$C_4$haloalkyl, $R_3$ is hydrogen, $C_1$–$C_4$alkyl or halogen and Q is $OR_{16}$ or $NH_2$ where $R_{16}$ is hydrogen or $C_1$–$C_4$-alkyl.

2. A compound of formula IIb

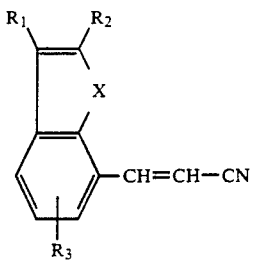

(IIb)

wherein X is oxygen or sulfur, $R_1$ is hydrogen, halogen, $C_1$–$C_4$alkyl or $C_1$–$C_4$haloalkyl, $R_2$ is hydrogen, halogen, $C_1$–$C_4$alkyl or $C_1$–$C_4$haloalkyl, $R_3$ is hydrogen, $C_1$–$C_4$alkyl or halogen.

* * * * *